United States Patent [19]

Baker et al.

[11] 4,069,382

[45] Jan. 17, 1978

[54] 9-(5-O-ACYL-β-D-ARABINOFURANOSYL) ADENINE COMPOUNDS

[75] Inventors: David Clarkston Baker; Theodore Herbert Haskell, both of Ann Arbor, Mich.

[73] Assignee: Parke, Davis & Company, Detroit, Mich.

[21] Appl. No.: 687,272

[22] Filed: May 17, 1976

[51] Int. Cl.² ............................................. C07H 19/18
[52] U.S. Cl. ....................................... 536/26; 424/180
[58] Field of Search ............................... 536/26, 27, 24

[56] References Cited

U.S. PATENT DOCUMENTS

| | | | |
|---|---|---|---|
| 3,309,358 | 3/1967 | Hanze | 536/27 |
| 3,457,253 | 7/1969 | Wechter | 536/27 |
| 3,651,045 | 3/1972 | Haskell et al. | 536/26 |

*Primary Examiner*—Johnnie R. Brown
*Attorney, Agent, or Firm*—David B. Ehrlinger; Stephen Raines; Frank S. Chow

[57] ABSTRACT

9-(5-O-Acyl-β-D-arabinofuranosyl)adenine compounds and their production by reacting 9-(β-D-arabinofuranosyl)adenine with a reactive derivative of an alkanoic acid. The compounds are useful as antiviral agents. The compounds are water-soluble and lipophilic, thereby being adaptable to a wide variety of pharmaceutical formulations.

9 Claims, No Drawings

9-(5-O-ACYL-β-D-ARABINOFURANOSYL)ADENINE COMPOUNDS

The present invention relates to new organic compounds that are useful in pharmacological agents and to a method for their production. More particularly, the invention relates to new 9-(5-O-acyl-β-D-arabinofuranosyl)-adenine compounds that are represented by the formula

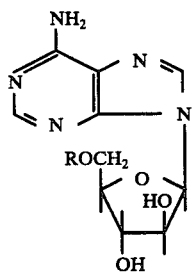

where R is a straight chain alkanoyl group having from 2 to 8 carbon atoms or a branched chain alkanoyl group having 4 to 5 carbon atoms. Examples of alkanoyl groups represented by R are acetyl, propionyl, butyryl, pentanoyl, hexanoyl, octanoyl, 3-methylbutyryl, and 2,2-dimethylpropionyl.

In accordance with the invention, 9-(5-O-acyl-β-D-arabinofuranosyl)adenine compounds having formula I are produced by reacting 9-(β-D-arabinofuranosyl)adenine with an equivalent quantity of a reactive derivative of an alkanoic acid that can be represented by the formula ROH where R is a straight chain alkanoyl group having from 2 to 8 carbon atoms or a branched chain alkanoyl group having 4 to 5 carbon atoms. Suitable reactive derivatives of the alkanoic acid that may be used for this purpose are the acid anhydride and an acid halide. When an acid halide, preferably an acid chloride, is used, a tertiary amine such as triethylamine, quinoline, N-methylpiperidine, or pyridine, is added to the reaction mixture in an amount sufficient to bind the hydrohalic acid liberated. When the acid anhydride is employed, it is preferable to add tertiary amine to the reaction mixture, such as one of those named above. The reaction is advantageously carried out in a tertiary amide solvent medium. Suitable solvents for this purpose include N,N-dimethylformamide, N,N-dimethylacetamide, and N-methyl-2-pyrrolidinone; as well as mixtures of these. A preferred base-solvent combination is a 1:1 mixture of pyridine and dimethylformamide. A large excess of this base-solvent mixture is used, in a preferred procedure, together with 1 to 1.2 equivalents of the acid chloride, based on the amount of 9-β-D-arabinofuranosyladenine used. The precise temperature and duration of the reaction are not critical and may be varied widely depending upon the reactants and solvent employed. When either an acid halide or the acid anhydride is used in the presence of tertiary amine, the reaction temperature can be varied between about 0° and about 100° C. for 1 to 24 hours, with the longer times being used at the lower temperatures. In most cases, preferred conditions are temperatures from 20° to 30° C. for 1.5 to 12 hours, although longer times as well as higher temperatures may be used to insure completeness of reaction. When an excess of the alkanoic acid derivative is used, the excess is decomposed at the conclusion of the reaction, by the addition of water, prior to isolation of the product.

The 9-(5-O-acyl-β-D-arabinofuranosyl)adenine compounds are new chemical compounds that are useful as pharmacological agents, especially as antiviral agents against herpes virus.

Their activity as antiviral agents can be quantitatively measured in an in vitro test by utilizing the plaque reduction technique first developed by Dulbecco (Proc. Natl. Acad. Sci., Volume 38, pages 747–752) and modified by Hsiung and Melnick (Virology, Volume 1, pages 533–535). In this test, a complete cell monolayer is first grown on a glass test unit. The growth medium is then removed, and the virus is adsorbed on the cell monolayer for a measured time period. In the absence of an antiviral agent, the virus will destroy well-defined areas of cells, called plaques, that can be seen macroscopically when the vital stain, neutral red, is added to the system. To test the inhibiting effect of a given compound, the test compound in solution is added to the virus-cell system, and the whole is covered with a nutrient agar overlay containing neutral red. After incubation, the plaques are counted, and the number of plaques produced in the system containing the test compound is compared with the number produced in the control systems, from whch only the test compound is omitted. The inhibitory activity of a test compound is reported as the percentage reduction of the plaque count on the test units compared with that on the controls.

When tested by this plaque reduction technique, with 4 oz. glass bottles serving as the test units and H. Ep. No. 2 cells making up the cell monolayer, the compounds of the invention, at a concentration of 50–65 micrograms/ml. in Hank's Balanced Salt Solution (pH 7–8), typically were found to give substantially complete plaque reduction against herpes simplex.

As specified above, the ester compounds of the invention are derived from 9-(β-D-arabinofuranosyl)adenine, which is known to be an antiviral agent that is active against herpes virus. The latter compound has been reported to be more active in vitro against herpes virus than its 5'-benzoyl ester whereas its 5'-palmitate ester was inactive in the same test (Renis et al., *J. Med. Chem.*, 16, 754); the compound has also been reported (Repta et al., *J. Pharm. Sci.*, 64, 392) to be poorly soluble in water and its 5'-formate ester, relatively water-soluble, to be unstable in aqueous solution. It is therefore surprising that the compounds of the invention, unlike the prior art compounds, exhibit good antiviral activity and are adaptable to a wide variety of oral, topical and parenteral pharmaceutical formulations, being readily soluble in water and/or lipophilic. Preferred compounds of the invention in this regard are the compounds of Formula I in which R is a straight chain alkanoyl group having from 2 to 8 carbon atoms and, in particular 9-(5-O-acetyl-β-D-arabinofuranosyl)adenine, 9-(5-O-propionyl-β-D-arabinofuranosyl)adenine, 9-(5-O-butyryl-β-D-arabinofuranosyl)adenine, and 9-(5-O-pentanoyl-β-D-arabinofuranosyl)adenine, of which latter compounds the 5-O-pentanoyl compound is the first compound of choice for its antiviral properties. Also preferred for their increased solubility properties and lipophilicity are 9-[5-O-(3-methylbutyryl)-β-D-arabinofuranosyl]adenine and 9-(5-O-butyryl-β-D-arabinofuranosyl)-adenine The invention is illustrated by the following examples.

EXAMPLE 1

To a stirred mixture of 2.67 g. of 9-(β-D-arabinofuranosyl)adenine and 100 ml. of 1:1 dimethylformamide-pyridine is added 0.79 g. of acetyl chloride at 25° C. The mixture is stirred, while being protected from moisture, for 1.5 hours, then treated with 50 g. of crushed ice and evaporated at reduced pressure. The residue is added to a 3 × 40 cm. column of dry silica gel and the column is eluted sequentially with 500-ml. portions of 5, 10, 15 and 20% (v/v) methanol in chloroform. Two fractions of eluate (the 15 and 20% methanol in chloroform eluates) are combined and evaporated at reduced pressure to give the desired product 9-(5-O-acetyl-β-D-arabinofuranosyl)adenine; m.p. 197.5°–198.5° C. after crystallization from ethanol, $[\alpha]_D^{23} = +23.6°$ (c = 1% in methanol), $\lambda_{max}^{CH_3OH} = 258$ nm ($\epsilon = 15,000$), water solubility: 9.9 mg./ml.

EXAMPLE 2

By substituting 1.11 g. of propionyl chloride for the acetyl chloride in Example 1 and stirring the reaction mixture for 12 hours the residual product obtained is 9-(5-O-propionyl-β-D-arabinofuranosyl)adenine; m.p. 201°–203° C. after crystallization from ethanol, $[\alpha]_D^{23} = +22.8°$, $\lambda_{max}^{CH_3OH} = 258$ nm ($\epsilon = 14,900$), water solubility: 9.2 mg./ml. (pH 7 buffer). The product contains 0.3 equivalent of ethanol of crystallization.

EXAMPLE 3

By substituting 1.2 g. of butyryl chloride for the acetyl chloride in Example 1 and stirring the reaction mixture for 3 hours the residual product obtained is 9-(5-O-butyryl-β-D-arabinofuranosyl)adenine; after crystallization from ethanol the product sinters at 184° C. and decomposes at 187°–189° C., $\lambda_{max}^{pH\ 7} = 259$ nm ($\epsilon = 15,100$), water solubility: 16.1 mg./ml.

EXAMPLE 4

By substituting 1.21 g. of pentanoyl chloride for the acetyl chloride in Example 1 and stirring the reaction mixture for 6 hours the residual product obtained is 9-(5-O-pentanoyl)-β-D-arabinofuranosyl)adenine containing 0.2 equivalent of water; water solubility: 8.4 mg./ml.

EXAMPLE 5

By substituting 1.55 g. of 3-methylbutyryl chloride for the acetyl chloride in Example 1 and stirring the reaction mixture for 12 hours the residual product obtained is 9-[5-O-(3-methylbutyryl)-β-D-arabinofuranosyl]-adenine containing 1.25 equivalents of water; $[\alpha]_D^{23} = +32.6°$ (C = 1% in methanol), $\lambda_{max}^{CH_3OH} = 258$ nm ($\epsilon = 14,700$), water solubility: 16.4 mg./ml.

EXAMPLE 6

2,2-Dimethylpropionyl chloride (1.45 g.) is added to a stirred mixture of 2.67 g. of 9-(β-D-arabinofuranosyl)-adenine and 100 ml. of 1:1 dimethylformamide-pyridine at 25° C. The mixture is stirred for 4 hours, then treated with 50 g. of crushed ice, and evaporated at reduced pressure. The residue is added to a 3 × 40 cm. column of dry silica gel and eluted sequentially with chloroform and/or tetrahydrofuran in the series, 100% chloroform, chloroform/tetrahydrofuran mixtures in a linear gradient up to 100% tetrahydrofuran, and finally 100% tetrahydrofuran. The fractions containing the desired product are combined and evaporated at reduced pressure. The product is 9-[5-O-(2,2-dimethylpropionyl)-β-D-arabinofuranosyl]-adenine, containing 0.2 equivalent of tetrahydrofuran; $[\alpha]_D^{23} = +35°$ (C = 1% in methanol, $\lambda_{max}^{CH_3OH} = 259$ nm ($\epsilon = 14,900$), water solubility: 7.0 mg./ml.

EXAMPLE 7

By substituting 1.40 g. of hexanoyl chloride for the acetyl chloride in the procedure of Example 1 and stirring the reaction mixture for 20 hours at 50° C., the product obtained in the workup is 9-(5-O-hexanoyl-β-D-arabinofuranosyl)adenine containing 0.2 equivalent of water; $\lambda_{max}^{CH_3OH} = 259$ nm ($\epsilon = 14,500$), water solubility: 2.5 mg./ml. (pH7 buffer), partition coefficient: 60.5 (pentanol/water).

By substituting 2.0 g. of octanoyl chloride for the acetyl chloride in the procedure of Example 1 and stirring the reaction mixture for 1.5 hours at 50° C., the product obtained is 9-(5-O-octanoyl)-β-D-arabinofuranoyl)-adenine; $[\alpha]_D^{23} = +29.4°$ (C = 1% in methanol), $\lambda_{max}^{CH_3OH} = 259$ nm ($\epsilon = 14,400$), partition coefficient: Ca. 100 (penanol/water).

We claim:

1. A 9-(5-O-acyl-β-D-arabinofuranosyl)adenine compound having the formula

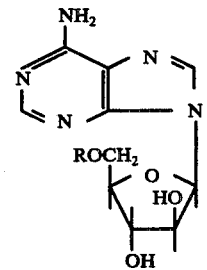

where R is a straight chain alkanoyl group having from 2 to 8 carbon atoms or a branched chain alkanoyl group having 4 to 5 carbon atoms.

2. A compound according to claim 1 which is 9-(5-O-acetyl-β-D-arabinofuranosyl)adenine.

3. A compound according to claim 1 which is 9-(5-O-propionyl-β-D-arabinofuranosyl)adenine.

4. A compound according to claim 1 which is 9-(5-O-butyryl-β-D-arabinofuranosyl)adenine.

5. A compound according to claim 1 which is 9-(5-O-pentanoyl-β-D-arabinofuranosyl)adenine.

6. A compound according to claim 1 which is 9-[5-O-(3-methylbutyryl)-β-D-arabinofuranosyl]adenine.

7. A compound according to claim 1 which is 9-[5-O-(2,2-dimethylpropionyl)-β-D-arabinofuranosyl]adenine.

8. A compound according to claim 1 which is 9-(5-O-hexanoyl-β-D-arabinofuranosyl)adenine.

9. A compound according to claim 1 which is 9-(5-O-octanoyl-β-D-arabinofuranosyl)adenine.

* * * * *